(12) United States Patent
Wring et al.

(10) Patent No.: US 11,911,382 B2
(45) Date of Patent: *Feb. 27, 2024

(54) METHOD FOR TREATING PULMONARY ARTERIAL HYPERTENSION AND ASSOCIATED PULMONARY ARTERIAL HYPERTENSION

(71) Applicant: Altavant Sciences GmbH, Basel (CH)

(72) Inventors: Steve Wring, South Boston, VA (US); Magdalena Alonso-Galicia, Durham, NC (US); Thomas Pack, Durham, NC (US); Julie Rurka, Raleigh, NC (US); David Carpenter, Durham, NC (US); Melissa Rhodes, Raleigh, NC (US)

(73) Assignee: Altavant Sciences GmbH (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/813,173

(22) Filed: Jul. 18, 2022

(65) Prior Publication Data

US 2023/0000866 A1 Jan. 5, 2023

Related U.S. Application Data

(63) Continuation of application No. 16/685,165, filed on Nov. 15, 2019, now Pat. No. 11,413,287.

(60) Provisional application No. 62/768,575, filed on Nov. 16, 2018.

(51) Int. Cl.
| | | |
|---|---|---|
| *A61K 31/506* | (2006.01) | |
| *A61K 9/00* | (2006.01) | |
| *A61P 9/00* | (2006.01) | |
| *A61P 9/12* | (2006.01) | |
| *A61P 11/00* | (2006.01) | |

(52) U.S. Cl.
CPC .......... *A61K 31/506* (2013.01); *A61K 9/0053* (2013.01); *A61P 9/12* (2018.01)

(58) Field of Classification Search
CPC .......... A61K 31/506; A61P 11/00; A61P 9/00; A61P 9/12
USPC ...................................................... 514/272
See application file for complete search history.

(56) References Cited

U.S. PATENT DOCUMENTS

| | | |
|---|---|---|
| 9,199,994 B2 | 12/2015 | De Lombaert et al. |
| 9,512,122 B2 | 12/2016 | De Lombaert et al. |
| 9,750,740 B2 | 9/2017 | De Lombaert et al. |
| 10,045,988 B2 | 8/2018 | De Lombaert et al. |
| 10,350,208 B2 | 7/2019 | De Lombaert et al. |
| 10,660,893 B2 | 5/2020 | De Lombaert et al. |
| 10,946,018 B2 | 3/2021 | De Lombaert et al. |
| 11,203,597 B2 * | 12/2021 | Patterson ............... A61K 9/007 |
| 11,413,287 B2 * | 8/2022 | Wring ...................... A61P 11/00 |
| 11,576,915 B2 * | 2/2023 | Alonso-Galicia ......... A61P 9/12 |
| 11,607,413 B2 | 3/2023 | Palacios et al. |
| 2015/0080393 A1 | 3/2015 | De Lombaert et al. |
| 2016/0096836 A1 | 4/2016 | De Lombaert et al. |
| 2017/0095476 A1 | 4/2017 | De Lombaert et al. |
| 2018/0092918 A1 | 4/2018 | De Lombaert et al. |
| 2018/0256574 A1 | 9/2018 | De Lombaert et al. |
| 2019/0282575 A1 | 9/2019 | De Lombaert et al. |
| 2020/0148681 A1 | 5/2020 | Patterson |
| 2020/0155552 A1 | 5/2020 | Wring et al. |
| 2020/0188398 A1 | 6/2020 | Pack et al. |
| 2020/0188399 A1 | 6/2020 | Pack et al. |
| 2020/0237759 A1 | 7/2020 | Palacios et al. |
| 2020/0237760 A1 | 7/2020 | De Lombaert et al. |
| 2020/0289510 A1 | 9/2020 | Alonso-Galicia et al. |
| 2022/0047594 A1 * | 2/2022 | Pack ....................... A61P 11/00 |
| 2022/0073516 A1 * | 3/2022 | Patterson ............... A61K 9/007 |
| 2022/0096475 A1 * | 3/2022 | Pack ..................... A61K 31/506 |
| 2023/0007425 A1 | 3/2023 | Wring et al. |

FOREIGN PATENT DOCUMENTS

| | | |
|---|---|---|
| WO | 2009009561 A1 | 1/2009 |
| WO | 2015035113 A1 | 3/2015 |
| WO | 2020099926 A1 | 5/2020 |
| WO | 2020099929 A1 | 5/2020 |
| WO | 2020128608 A1 | 6/2020 |
| WO | 2020157577 A1 | 8/2020 |
| WO | 2020188352 A1 | 9/2020 |

(Continued)

OTHER PUBLICATIONS

Diaz-Guzman et al., "Pulmonary Hypertension Caused by Sarcoidosis", Clin. Chest Med., 2008, 29(3);549-563.
International Preliminary Report on Patentability issued in international application PCT/IB2019/001224, 8 pages, dated May 18, 2021.
Aiello et al: "Tryptophan hydroxylase 1 Inhibition Impacts Pulmonary Vascular Remodeling in Two Rat Models of Pulmonary Hypertension" Journal of Pharmacology and Experimental Therapeutics, vol. 360, No. 2, p. 267-279, Jan. 6, 2017.

(Continued)

*Primary Examiner* — Raymond J Henley, III
(74) *Attorney, Agent, or Firm* — Fox Rothschild LLP

(57) ABSTRACT

There is a method of treating or preventing pulmonary arterial hypertension or associated pulmonary arterial hypertension in a patient. The method has the step of systemically administering to the patient a therapeutically effective amount of one or more compounds: (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate or a pharmaceutically acceptable salt thereof, or (S)-8-(2-amino-6-((R)-1-(5-chloro-[1,1'-biphenyl]-2-yl)-2,2,2-trifluoroeth-oxy)pyrimidin-4-yl)-2,8-diazaspiro[4.5]decane-3-carboxylic acid or a pharmaceutically acceptable salt thereof, or a combination of the foregoing. There is also a method of treating or preventing pulmonary arterial hypertension or associated pulmonary arterial hypertension in a patient by systemically administering a therapeutically effective amount of a THP1 inhibitor from about 1 mg/kg/day to about 50 mg/kg/day.

8 Claims, 2 Drawing Sheets

(56) References Cited

FOREIGN PATENT DOCUMENTS

| WO | 2021152398 A1 | 8/2021 |
|---|---|---|
| WO | 2023/079486 | 5/2023 |

OTHER PUBLICATIONS

Paralkar et al: "KAR5585, a first-in-class oral tryptophan hydroxylase 1 (TPH1) inhibitor as a novel candidate or the treatment of pulmonary arterial hypertension" American Journal of Respiratory and Critical Care Medicine, American Thoracic Society, United States, vol. 195, Jan. 1, 2017.

U S: "Guidance for Industry Estimating the Maximum Safe Starting Dose in Initial Clinical Trials for Therapeutics in Adult Healthy Volunteers Department of Health and Human Services Food and Drug Administration Center for Drug Evaluation and Research (CDER)", FDA Guidelines, Jul. 1, 2005, table 1, p. 26, Jul. 1, 2005.

Wring et al: "Safety, tolerability, pharmacokinetics and pharmacodynamics after repealed once or twice daily RUT-1201, a TPH inhibitor for treatment of PAH", European Respiratory Journal Sep. 1, 2019 European Respiratory Society NLD, vol. 54, No. Supplement 63, Sep. 1, 2019.

International Search Report and Written Opinion issued in international application PCT/IB2019/001224, 15 pages, dated Apr. 23, 2020.

Lau et al., "The Role of Circulating Serotonin in the Development of Chronic Obstructive Pulmonary Disease" PloS One,e31617, 7 (2012).

Egermayer et al., "Role of Serotonin in the Pathogenesis of Acute and Chronic Pulmonary Hypertension," Thorax, 1999, 54(2):161-168.

International Preliminary Report on Patentability issued in international application PCT/IB2020/000074, 8 pages, dated Jul. 27, 2021.

Bader et al., "Inhibition of serotonin synthesis: A novel therapeutic paradigm," Pharmacology & Therapeutics, 2020, vol. 205; 107423 (11 pages).

International Search Report issued in international application PCT/IB2020/000074, 6 pages, dated Jun. 26, 2020.

Written Opinion of the International Search Authority issued in international application PCT/IB2020/000074, 9 pages, dated Jun. 26, 2020.

Mawe et al, "Serotonin signaling in the gut—functions, dysfunctions and therapeutic targets," Nat. Rev. Gastroenterology & Hepatology, Aug. 2013, 10:473-486.

Gershon, M. D., "5-hydroxytryptamine (serotonin) in the Gastrointestinal Tract". Current Opinion in Endocrinology, Diabetes, and Obesity 20, 14-21 (2013).

Lesurtel et al., "Role of Serotonin in the Hepato-gastroIntestinal Tract: An Old Molecule for New Perspectives," Cell. Mol. Life Sci., 2008 65:940-952.

Kode et al., "FOXO1 orchestrates the bone-suppressing function of gut-derived serotonin," J. Clinical Investigation, Jul. 2012 (14 pages).

Yadav et al., "Pharamacological inhibition of gut-derived serotonin synthesis is a potential bone anabolic treatment for osteoporosis," Nature Medicine, Feb. 2010, 1-14.

Yadav et al., "Lrp5 Controls Bone Formation by Inhibiting Serotonin Synthesis in the Duodenum," Cell, Nov. 2008, 135:825-837.

Liang et al., "Serotonin Promotes the Proliferation of Serum-deprived Hepatocellular Carcinoma Cells via Upregulalion of FOXO3a," Molecular Cancer, 2013, 12:14 (11 pages).

Soll et al., "Serotonin Promotes Tumor Growth in Human Hepatocellular Cancer," Hepalology 2010, 51(4):1244-1254.

Pai et al., "Altered serotonin physiology in human breast cancers favors paradoxical growth and cell survival," Breast Cancer Research, Nov. 2009, 11(6): 1-17.

Engelman et al., "Inhibition of Serotonin Synthesis by Para-chlorophenylalanine in Patients With the Carcinoid Syndrome," The New England Journal of Medicine, Nov. 1967, 277: 1103-1108.

Sumara et al., "Gut-derived Serotonin is a Multifunctional Determinant to Fasting Adaptation," Cell Metabolism, Nov. 2012, 16:1-13.

Ban et al., "Impact of Increased Plasma Serotonin Levels and Carotid Atherosclerosis on Vascular Dementia," Atherosclerosis, 2007, 195:153-159.

Manocha et al.,"Serotonin and GI Disorders: An Update on Clinical and Experimental Studies," Clinical and Translational Gastroenterology, 2012, 3:e13, 6 pages.

Ghia et al., "Serotonin has a key role in pathogenesis of experimental colitis," Gastroenterology, 2009, 137(5): 1649-1660.

Sikander et al., "Role of serotonin in gastrointestinal motility and irritable bowel syndrome," Clinical Chimica Acta, 2009, 403:47-55.

Galligan et al. "Recent advances in understanding the role of serotonin in gastrointestinal motility and functional bowel disorders," Neurogastroenterol Motil., 2007, 19(Suppl.2):1-4.

Costedio et al., "Serotonin and Its Role in Colonic Function and in Gastrointestinal Disorders," Diseases of the Colon and Rectum, Mar. 2007, 50(3): 376-88.

Gershon and Tack, "The Serotonin Signaling System: From Basic Understanding to Drug Development for Functional GI Disorders," Gastroenterology, 2007, 132(1):397-414.

Mawe et al., "Review article: Intestinal Serotonin Signaling in Irritable Bowel Syndrome," Aliment Pharmacol. Ther., 2006, 23(8): 1067-1076.

Duerschmied et al., "Platelet Serotonin Promotes the Recruitment of Neutrophils to Sites of Acute Inflammation in Mice," Blood, Feb. 2013, 121(6):1008-1015.

Li et al., "Serotonin Activates Dendritic Cell Function in the Context of Gut Inflammation," The American Journal of Pathology, Feb. 2011, 178(2):662-671.

Ebrahimkhani et al., "Stimulating Healthy Tissue Regeneration by Targeting the 5-HT2B Receptor in Chronic Liver Disease," Nature Medicine, 2011 17, 1668-1673.

Wacker et al., "Structural Features for Functional Selectivity at Serotonin Receptors," Science, May 2013, 340(6132):615-619.

Stokes et al., "p-Ethynylphenylalanine: A Potent Inhibitor of Tryptophan Hydroxylase," J. Neurochemistry, 2000, 74(5):2067-2073.

Zhong et al., "Molecular Dynamics Simulation of Tryptophan Hydroxylase-1: Binding Modes and Free Energy Analysis to Phenylalanine Derivative Inhibitors," Int. J Molecular Sci, May 2013, 14:9947-9962.

Camilleri, "LX-1031, A Tryptophan 5-hydroxylase Inhibitor, and Its Potential in Chronic Diarrhea Associated With Increased Serotonin," Neurogastroenterol Motil., Mar. 2011, 23(3):193-200.

Cianchetta et al., "Mechanism of Inhibition of Novel Tryptophan Hydroxylase Inhibitors Revealed by Co-crystal Structures and Kinetic Analysis," Current Chemical Genomics, 2010, 4:19-26.

Jin et al., "Substituted 3-(4-(1,3,5-triazin-2-yl)-phenyl)-2-aminopropanoic Acids as Novel Tryptophan Hydroxylase Inhibitors," Bioorganic & Medicinal Chemistry Letters, 2009, 19:5229-5232.

Shi et al., "Modulation of Peripheral Serotonin Levels by Novel Tryptophan Hydroxylase Inhibitors or the Potential Treatment of Functional Gastrointestinal Disorders," J Med Chem, 2008, 51:3684-3687.

Liu et al., "Discovery and Characterization of Novel Tryptophan Hydroxylase Inhibitors That Selectively Inhibit Serotonin Synthesis in the Gastrointestinal Tract," J. Pharrnacol. Exp. Ther, 2008, 325(1):47-55.

Margolis et al., "Pharmacological Reduction of Mucosal but Not Neuronal Serotonin Opposes Inflammation in Mouse Intestine," Gut, Jun. 2013, 1-10 (with Supplemental Information).

Ouyang et al., "Combined Structure-Based Pharmacophore and 3D-QSAR Studies on Phenylalanine Series Compounds as TPII 1 Inhibitors," Int J Molecular Sci, 2012, 13:5348-5363.

Robiolio et al., "Carcinoid Heart Disease: Correlation of High Serotonin Levels with Valvular Abnormalities Detected by Cardiac Catheterization and Echocardiography," Circulation, 1995, 92:790-795.

International Preliminary Report on Patentability issued in international application, PCT/IB2020/000177, 10 pages, dated Sep. 16, 2021.

(56) References Cited

OTHER PUBLICATIONS

International Search Report and Written Opinion issued in international application, PCT/IB2020/000177, 17 pages, dated Sep. 1, 2020.
Crowell, M.D. "Role of Serotonin in the Pathophysiology of the Irritable Bowel Syndrome," British Journal of Pharmacology, 2004, 141(8):1285-93.
Lazarus, Howard et al. ELEVATE 2: A multicenter study of rodatristat ethyl in patients with WHO Group 1 pulmonary arterial hypertension (PAH), European Respiratory Society, Sep. 5, 2021 (Sep. 5, 2021), pp. 1-5.
Blalock, Shannon et al., "Long-Term Outcomes With Ambrisentan Monotherapy in Pulmonary Arterial Hypertension", Journal of Cardiac Failure, Churchill Livingstone, Naperville, IL, US, vol. 16, No. 2, Feb. 1, 2010 (Feb. 1, 2010), pp. 121-127.
Johnson, B. et al., "A Pharmacokinetic/Pharmacodynamic Based Rationale for Dose Selection of the TPH Inhibitor Rodatristat Ethyl in ELEVATE-2—a Phase 2b Study in Pulmonary Arterial Hypertension", Abstract, TP82. TP082 Let It Be, Clinical Advances in Pulmonary Vascular Disease: PAH and Beyond, May 1, 2021 (May 1, 2021), pp. A3604-A3604, XP093025115, DOI: 10.1164/ajrccm-conference.2021.203.1 MeetingAbstracts. A3604 Retrieved from the Internet: URL:http://dx.doi.org/10.1164/ajrccm-conference, 1 page.
Palacios M. et al., "Rodatristat Ethyl Monotherapy and Combination with Ambrisentan Reverses Incidence of Vascular Occlusions to Baseline Normoxic Levels in the Rat SUGEN-Hypoxia Model of Pulmonary Arterial Hypertension", Abstract, C56. Cow Hollow: Preclinical Models of Pulmonary Hypertension, May 1, 2022 (May 1, 2022), pp. A4440-A4440, XP093025079, DOI: 10.1164/ajrccm-conference.2022.205.1_MeetingAbstracts. A4440 Retrieved from the Internet: URL:http://dx.doi.org/10.1164/ajrccm-conference, 1 page.
International Search Report and Written Opinion dated Feb. 27, 2023 in PCT Application No. PCT/IB2022/060605, 16 pages.
Altavant Sciences: "Altavant Sciences to Present Data Supporting Planned Phase 2 Clinical Program for Rodatristat Ethyl in Patients with Pulmonary Arterial Hypertension at PVRI World Congress", Cision PR Newswire, Jan. 31, 2019 (Jan. 31, 2019), XP055810161, Retrieved from the Internet <URL:https://www.prnewswire.com/news-releases/altavant-sciences-to-present-data-supporting-planned-phase-2-clinical-program-for-rodatristat-ethyl-in-patients-with-pulmonary-arterial-hypertension-at-pvri-world-congress-300787225.html>, 3 pages.
Anonymous: "NCT03924154: A Study of RVT-1201 in Patients With Pulmonary Arterial Hypertension (ELEVATE 1)", Jan. 28, 2020 (Jan. 28, 2020), XP055810004, Retrieved from the Internet <URL:https://clinicaltrials.gov/ct2/history/NCT03924154?V_9=View#StudyPageTop>, 8 pages.
Carpenter D et al: "Once daily oral dosing of rodatristat ethyl (rvt-1201) achieves reductions in serotonin biosynthesis comparable to those associated with reversal of vascular remodeling in pah animal models", Chest, American College of Chest Physicians, US, vol. 156, No. 4, Supplement, Oct. 2019 (Oct. 1, 2019), pp. A1175-A1176, XP009519736, ISSN: 0012-3692, DOI: 10.1016/J.CHEST.2019.08.1068.
Lajoie Annie-Christine et al: "Combination therapy in pulmonary arterial hypertension: recent accomplishments and future challenges", Pulmonary Circulation Apr.-Jun. 2012, vol. 7, No. 2, Jun. 2017 (Jun. 1, 2017), pp. 312-325, XP055810165, ISSN: 2045-8940, DOI: 10.1177/2045893217710639.
International Search Report and Written Opinion dated Jun. 17, 2021, in International Application No. PCT/IB2021/000046, 12 pages.

\* cited by examiner

METHOD FOR TREATING PULMONARY ARTERIAL HYPERTENSION AND ASSOCIATED PULMONARY ARTERIAL HYPERTENSION

CROSS-REFERENCE TO RELATED APPLICATION APPLICATIONS

This Application is a Continuation of U.S. application Ser. No. 16/685,165 filed on Nov. 15, 2019, which claims priority to U.S. Provisional Application No. 62/768,575, filed Nov. 16, 2018, the contents of all of which are incorporated herein in their entireties.

BACKGROUND OF THE DISCLOSURE

1. Field of the Disclosure

The present disclosure relates to a method for treating pulmonary arterial hypertension (PAH) and associated pulmonary arterial hypertension (APAH) in a patient. The present disclosure further relates to a method for treating PAH/APAH via a systemic administration to a patient.

2. Description of the Prior Art

Pulmonary arterial hypertension (PAH) is one form of a broader condition known as pulmonary hypertension, which means high blood pressure in the lungs. In PAH, increased pressure in the vessels is caused by obstruction in small arteries in the lungs and/or constriction or narrowing in diameter, which increases the resistance to blood flow through the lungs. Over time, the increased blood pressure can damage the heart. In many cases of pulmonary arterial hypertension, the cause is unknown. Others causes can be drug-related, HIV infection, and connective tissue/autoimmune disorders (such as scleroderma).

A type of PAH is associated pulmonary arterial hypertension (APAH). APAH can be PAH associated with other medical conditions including, for example, (1) collagen vascular disease (or connective tissue disease) which include autoimmune diseases such as scleroderma or lupus; (2) congenital heart and lung disease; (3) portal hypertension (e.g., resulting from liver disease); (4) HIV infection; (5) drugs (e.g., appetite suppressants, cocaine, and amphetamines; (6) other conditions including thyroid disorders, glycogen storage disease, Gaucher disease, hereditary hemorrhagic telangiectasia, hemoglobinopathies, myeloproliferative disorders, and splenectomy. APAH can also be PAH associated with abnormal narrowing in the pulmonary veins and/or capillaries such as in pulmonary veno-occlusive disease (PVOD) and pulmonary capillary hemangiomatosis.

Serotonin (5-hydroxytryptamine, 5-HT) is a neurotransmitter that modulates central and peripheral functions by acting on neurons, smooth muscle, and other cell types. 5-HT is involved in the control and modulation of multiple physiological and psychological processes, including in lung and pulmonary diseases. The literature discloses the relationship between 5-HT and pulmonary diseases at *PloS One*, e31617 7, (2012), "The Role of Circulating Serotonin in the Development of Chronic Obstructive Pulmonary Disease" and *Thorax* 161-168, 54 (1999), "Role of Serotonin in the Pathogenesis of Acute and Chronic Pulmonary Hypertension".

The rate-limiting step in 5-HT biosynthesis is the hydroxylation of tryptophan by dioxygen, which is catalyzed by tryptophan hydroxylase (TPH; EC 1.14.16.4) in the presence of the cofactor (6R)-L-erythro-5,6,7,8-tetrahydrobiopterin (BH4). The resulting oxidized product, 5-hydroxy tryptophan (5-HTT) is subsequently decarboxylated by an aromatic amino acid decarboxylase (AAAD; EC 4.1.1.28) to produce 5-HT. Together with phenylalanine hydroxylase (PheOH) and tyrosine hydroxylase (TH), TPH belongs to the pterin-dependent aromatic amino acid hydroxylase family.

Two vertebrate isoforms of TPH, namely TPH1 and TPH2, have been identified. TPH1 is primarily expressed in the pineal gland and non-neuronal tissues, such as entei chromaffin (EC) cells located in the gastrointestinal (GI) tract. TPH2 (the dominant form in the brain) is expressed exclusively in neuronal cells, such as dorsal raphe or myenteric plexus cells. The peripheral and central systems involved in 5-HT biosynthesis are isolated, with 5-HT being unable to cross the blood-brain barrier. Therefore, the pharmacological effects of 5-HT can be modulated by agents affecting TPH in the periphery, mainly TPH1 in the gut.

WO 2015/035113 and U.S. Pat. No. 9,199,994 disclose spirocyclic compounds that act as inhibitors of THP and are useful in the treatment of various diseases and disorders associated with peripheral serotonin, including cardiovascular diseases of pulmonary arterial hypertension (PAH) and associated pulmonary arterial hypertension (APAH).

However, there is a need for a method of treating or preventing PAH/APAH in a patient. There is further a need for a method of treating or preventing PAH/APAH in a patient with a systemic administration of a pharmaceutical compound or composition effective in modulating or ameliorating the effects of PAH/APAH. There is yet further a need for a method of treating or preventing PAH/APAH in a patient with a pharmaceutical compound or composition containing a THP1 inhibitor.

SUMMARY OF THE DISCLOSURE

According to the present disclosure, there is provided a method of treating or preventing PAH/APAH in a patient. The method has the step of administering to the patient a therapeutically effective amount of a compound selected from the group consisting of (i) (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate, (ii) (S)-8-(2-amino-6-((R)-1-(5-chloro-[1,1'-biphenyl]-2-yl)-2,2,2-trifluoroeth-oxy)pyrimidin-4-yl-2,8-diazaspiro[4.5]decane-3-carboxylic acid, and (iii) a combination of the foregoing. The therapeutically effective amount of the compound ranges from about 10 mg/kg/day to about 1000 mg/kg/day.

According to the present disclosure, there is provided a method of treating or preventing PAH/APAH in a patient. The method has the step of administering to the patient a therapeutically effective amount of a composition including a compound selected from the group consisting of (i) (S)-ethyl 8-(2-amino-6-((R)-1-(5-chloro-[1,1'-biphenyl]-2-yl)-2,2,2-trifluoroethoxy)pyrimidin-4-yl-2,8-diazaspiro[4.5]decane-3-carboxylate, (ii) (S)-8-(2-amino-6-((R)-1-(5-chloro-[1,1'-biphenyl]-2-yl)-2,2,2-trifluoroeth-oxy)pyrimidin-4-yl)-2,8-diazaspiro[4.5]decane-3-carboxylic acid, and (iii) a combination of the foregoing, together with one or more pharmaceutically acceptable excipients. The therapeutically effective amount of the compound ranges from about 10 mg/kg/day to about 1000 mg/kg/day.

According to the present disclosure, there is provided a method of treating or preventing PAH/APAH in a patient. The method has the step of administering to the patient a composition including a therapeutically effective amount of a compound selected from the group consisting of (i) (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate or a pharmaceutically acceptable salt thereof, (ii) (S)-8-(2-amino-6-((R)-1-(5-chloro-[1,1'-biphenyl]-2-yl)-2,2,2-trifluoroeth-oxy)pyrimidin-4-yl)-2,8-diazaspiro[4.5]decane-3-carboxylic acid or a pharmaceutically acceptable salt thereof, and (iii) a combination of the foregoing and a pharmaceutically acceptable excipient. The therapeutically effective amount of the compound ranges from about 10 mg/kg/day to about 1000 mg/kg/day.

According to the present disclosure, there is provided the use of a therapeutically effective amount of a compound in treating PAH/APAH. The compound is selected from the group consisting of (i) (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate or a pharmaceutically acceptable salt thereof and (ii) (S)-8-(2-amino-6-((R)-1-(5-chloro-[1,1'-biphenyl]-2-yl)-2,2,2-trifluoroeth-oxy)pyrimidin-4-yl)-2,8-diazaspiro[4.5]decane-3-carboxylic acid or a pharmaceutically acceptable salt thereof, and (iii) a combination of the foregoing. The therapeutically effective amount of the compound ranges from about 10 mg/kg/day to about 1000 mg/kg/day.

According to the present disclosure, there is provided a method of treating or preventing PAH/APAH in a patient. The method has the step of administering to the patient a therapeutically effective amount of a compound selected from the group consisting of (i) (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate or a pharmaceutically acceptable salt thereof, (ii) (S)-8-(2-amino-6-((R)-1-(5-chloro-[1,1'-biphenyl]-2-yl)-2,2,2-trifluoroeth-oxy)pyrimidin-4-yl)-2,8-diazaspiro[4.5]decane-3-carboxylic acid or a pharmaceutically acceptable salt thereof, and (iii) a combination of the foregoing.

According to the present disclosure, there is provided a method of treating or preventing PAH/APAH in a patient. The method has the step of administering to the patient a therapeutically effective amount of a THP1 inhibitor from about 1 mg/kg/day to about 50 mg/kg/day.

BRIEF DESCRIPTION OF THE DRAWINGS

Embodiments of the present disclosure are described herein with reference to the following figures.

DETAILED DESCRIPTION OF THE DISCLOSURE

Figure 1:
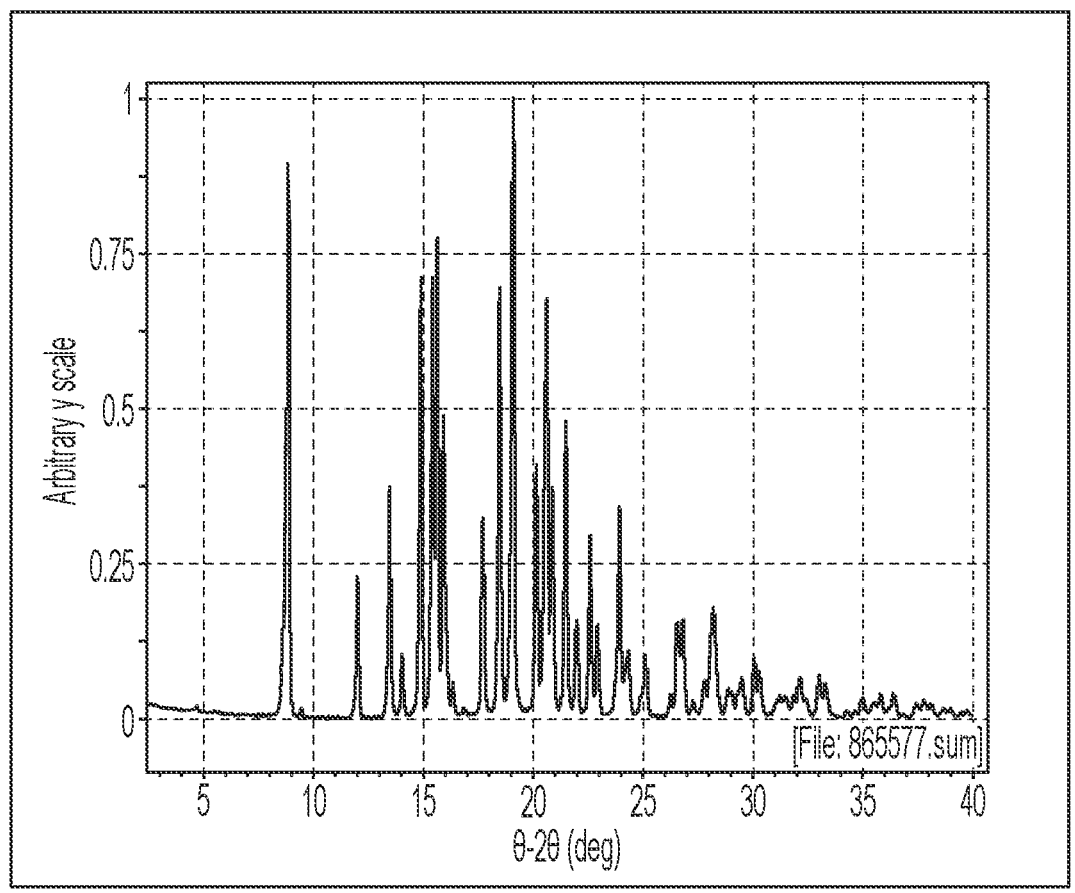
FIG. 1 is a plot of an XRPD of a crystalline compound of (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate according to the present disclosure (crystalline Form 3).

Pulmonary arterial hypertension (PAH) and associated pulmonary arterial hypertension (APAH) is treated via administration of either or both of two spirocyclic compounds. Without being bound to any theory, each of the two spirocyclic compounds act to inhibit the formation of 5-HT, and, thus, diminish or ameliorate effects of PAH/APAH.

A useful spirocyclic compound is (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate (also referred to herein as "RVT-1201"). The compound has the following formula:

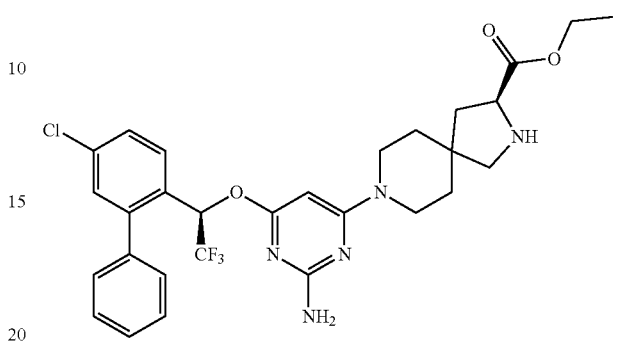

The above-referenced compound can be used to prevent or treat PAH/APAH in either an amorphous or crystalline form. Two different polymorph crystalline forms are identified by x-ray powder diffraction patterns set forth in FIG. 1 (Form 3) and FIG. 2 (Form 1) as well as Tables 1 and 2 (Form 3) and Tables 3 and 4 (Form 1). The crystalline Form 3 polymorph might be preferred, as it exhibits substantially greater stability and shelf life compared to the crystalline Form 1 polymorph, particularly at temperatures of less than 95° C.

TABLE 1

Observed Peaks for X-ray Powder Diffraction Pattern for Compound RVT-1201, Crystalline Form 3

| Peak position (°2θ) | d space (Å) | Intensity (%) |
|---|---|---|
| 8.78 ± 0.20 | 10.077 ± 0.235 | 90 |
| 12.00 ± 0.20 | 7.375 ± 0.125 | 25 |
| 13.47 ± 0.20 | 6.573 ± 0.099 | 39 |
| 14.02 ± 0.20 | 6.316 ± 0.091 | 12 |
| 14.87 ± 0.20 | 5.956 ± 0.081 | 71 |
| 15.39 ± 0.20 | 5.757 ± 0.075 | 72 |
| 15.61 ± 0.20 | 5.677 ± 0.073 | 78 |
| 15.89 ± 0.20 | 5.576 ± 0.071 | 50 |
| 16.31 ± 0.20 | 5.434 ± 0.067 | 7 |
| 17.70 ± 0.20 | 5.011 ± 0.057 | 34 |
| 18.45 ± 0.20 | 4.809 ± 0.052 | 70 |
| 19.05 ± 0.20 | 4.658 ± 0.049 | 100 |
| 20.12 ± 0.20 | 4.413 ± 0.044 | 42 |
| 20.57 ± 0.20 | 4.317 ± 0.042 | 68 |
| 20.84 ± 0.20 | 4.262 ± 0.041 | 39 |
| 21.46 ± 0.20 | 4.141 ± 0.039 | 49 |
| 21.94 ± 0.20 | 4.051 ± 0.037 | 18 |
| 22.56 ± 0.20 | 3.941 ± 0.035 | 31 |
| 22.90 ± 0.20 | 3.884 ± 0.034 | 17 |
| 23.90 ± 0.20 | 3.723 ± 0.031 | 35 |
| 24.32 ± 0.20 | 3.660 ± 0.030 | 13 |
| 25.07 ± 0.20 | 3.552 ± 0.028 | 12 |
| 26.54 ± 0.20 | 3.359 ± 0.025 | 17 |
| 26.76 ± 0.20 | 3.332 ± 0.025 | 18 |
| 27.79 ± 0.20 | 3.210 ± 0.023 | 8 |
| 28.21 ± 0.20 | 3.163 ± 0.022 | 19 |
| 29.48 ± 0.20 | 3.030 ± 0.020 | 9 |

TABLE 2

Prominent Observed Peaks for X-ray Powder Diffraction Pattern for Compound RVT-1201, Crystalline Form 3

| Peak position (°2θ) | d space (Å) | Intensity (%) |
|---|---|---|
| 8.78 ± 0.20 | 10.077 ± 0.235 | 90 |
| 14.87 ± 0.20 | 5.956 ± 0.081 | 71 |
| 15.39 ± 0.20 | 5.757 ± 0.075 | 72 |
| 15.61 ± 0.20 | 5.677 ± 0.073 | 78 |
| 18.45 ± 0.20 | 4.809 ± 0.052 | 70 |
| 19.05 ± 0.20 | 4.658 + 0.049 | 100 |

In yet another aspect, the Form 3 crystalline polymorph exhibits a characteristic XRPD peak at 19.05±0.20 (°2θ).

The Form 1 crystalline compound exhibits the XRPD (X-ray powder diffraction) pattern set forth below in Table 3.

TABLE 3

Observed Peaks for X-Ray Powder Diffraction Pattern for Compound RVT-1201, Crystalline Form 1

| Peak position (°2θ) | d space (Å) | Intensity (%) |
|---|---|---|
| 5.92 ± 0.20 | 14.936 ± 0.522 | 27 |
| 9.01 ± 0.20 | 9.816 ± 0.222 | 11 |
| 9.68 ± 0.20 | 9.140 ± 0.192 | 9 |
| 10.38 ± 0.20 | 8.523 ± 0.167 | 9 |
| 10.95 ± 0.20 | 8.082 ± 0.150 | 30 |
| 11.85 ± 0.20 | 7.468 ± 0.128 | 6 |
| 12.90 ± 0.20 | 6.861 ± 0.108 | 43 |
| 13.89 ± 0.20 | 6.376 ± 0.093 | 65 |
| 14.62 ± 0.20 | 6.057 ± 0.084 | 31 |
| 15.04 ± 0.20 | 5.890 ± 0.079 | 44 |
| 15.41 ± 0.20 | 5.750 ± 0.075 | 38 |
| 17.13 ± 0.20 | 5.176 ± 0.061 | 30 |
| 17.83 ± 0.20 | 4.974 ± 0.056 | 37 |
| 18.72 ± 0.20 | 4.741 ± 0.051 | 14 |
| 19.44 ± 0.20 | 4.567 ± 0.047 | 100 |
| 19.79 ± 0.20 | 4.487 ± 0.045 | 30 |
| 20.11 ± 0.20 | 4.417 ± 0.044 | 97 |
| 20.34 ± 0.20 | 4.366 ± 0.043 | 44 |
| 20.84 ± 0.20 | 4.262 ± 0.041 | 14 |
| 21.41 ± 0.20 | 4.151 ± 0.039 | 10 |
| 21.88 ± 0.20 | 4.063 ± 0.037 | 11 |
| 22.28 ± 0.20 | 3.991 ± 0.036 | 25 |
| 22.83 ± 0.20 | 3.895 ± 0.034 | 60 |
| 23.85 ± 0.20 | 3.731 ± 0.031 | 13 |
| 24.40 ± 0.20 | 3.648 ± 0.030 | 9 |
| 25.45 ± 0.20 | 3.500 ± 0.027 | 9 |
| 25.97 ± 0.20 | 3.431 ± 0.026 | 12 |
| 27.22 ± 0.20 | 3.276 ± 0.024 | 15 |
| 27.58 ± 0.20 | 3.235 ± 0.023 | 23 |
| 28.06 ± 0.20 | 3.180 ± 0.022 | 12 |
| 28.66 ± 0.20 | 3.115 ± 0.021 | 7 |

In still another aspect, the Form 1 crystalline compound exhibits prominent XRPD peaks set forth below in Table 4.

TABLE 4

Prominent Observed Peaks for X-Ray Powder Diffraction Pattern for Compound RVT-1201, Crystalline Form 1

| Peak position (°2θ) | d space (Å) | Intensity (%) |
|---|---|---|
| 12.90 ± 0.20 | 6.861 ± 0.108 | 43 |
| 13.89 ± 0.20 | 6.376 ± 0.093 | 65 |
| 15.04 ± 0.20 | 5.890 ± 0.079 | 44 |
| 19.44 ± 0.20 | 4.567 ± 0.047 | 100 |
| 20.11 ± 0.20 | 4.417 ± 0.044 | 97 |
| 20.34 ± 0.20 | 4.366 ± 0.043 | 44 |
| 22.83 ± 0.20 | 3.895 ± 0.034 | 60 |

The amorphous form of the RVT-1201 compound can be prepared by the method set forth in Example 63i of U.S. Pat. No. 9,199,994 (corresponding to WO2015/054202), which is incorporated by reference herein in its entirety. The amorphous form can then be converted to crystalline form by extraction with organic solvents, such as C4 to C10 alcohols, C4 to C10 alkyl acetates, and ethers. Useful alcohols include pentane, hexane, and heptane. A useful ether is methyl tert butyl ether (MTBE). By way of example, crystalline form 1 can be prepared by extraction with isopropanol, ethanol, cyclohexane, ethyl acetate, acetone, water, and mixtures of the foregoing, while crystalline Form 3 can be prepared by extraction with MTBE and/or heptane. Crystalline Forms 1 and 3 can be prepared by the extraction techniques set forth in U.S. Provisional Application No. 62/767,171, filed Nov. 14, 2018, which is incorporated by reference herein in its entirety.

Another useful spirocyclic compound is (S)-8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylic acid (herein alternately referred to as "KAR5417") of the following formula:

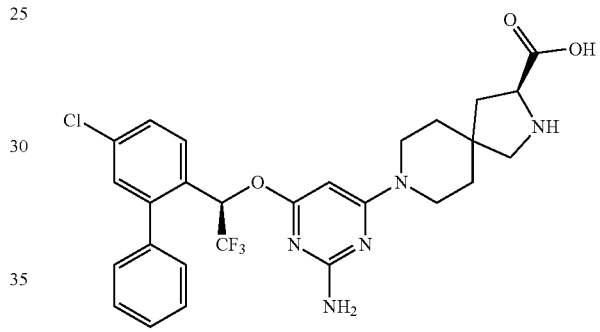

The amorphous form of the KAR5417 compound can be prepared by the method set forth in Example 34c of U.S. Pat. No. 9,199,994.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The efficacy of amorphous (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate in inhibiting TPH1 in mice was demonstrated in U.S. Pat. No. 9,199,994 in biological assays at Example 63i and Table 27.

As used herein, the term "patient" is used interchangeably, refers to any animal, including mammals, preferably mice, rats, other rodents, rabbits, dogs, cats, swine, cattle, sheep, horses, or primates, and, most preferably, humans. Humans are inclusive of humans of any age, including adults and children, including infants.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to 1) inhibiting the disease; for example, inhibiting a disease, condition or disorder in an individual who is experiencing or displaying the pathology or symptomatology of the disease, condition or disorder (i.e., arresting further development of the pathology and/or symptomatology), or 2) ameliorating the disease; for example, ameliorating a disease, condition or disorder in an individual who is experiencing or displaying the pathology or symptomatology of the disease, condition or disorder (i.e., reversing the pathology and/or symptomatology).

As used herein, the term "preventing" or "prevention" refers to reducing risk incidence, delaying, or inhibiting the onset or worsening of the disease; for example, in an individual who may be predisposed to the disease, condition or disorder but does not yet experience or display the pathology or symptomatology of the disease, or an individual who has previously suffered from the disease, condition or disorder, but has been treated and, e.g., no longer displays the pathology or symptomatology of the disease.

The spirocyclic compounds can be administered to patients (animals or humans) in need of such treatment in appropriate dosages that will provide prophylactic and/or therapeutic efficacy. The dose required for use in the treatment or prevention of any particular disease or disorder will typically vary from patient to patient depending on, for example, particular compound or composition selected, the route of administration, the nature of the condition being treated, the age and condition of the patient, concurrent medication or special diets then being followed by the patient, and other factors. The appropriate dosage can be determined by the treating physician; however, the dosage will be within the parameters defined herein.

The spirocyclic compounds can be administered systemically orally, subcutaneously, parenterally, by inhalation spray or rectally in dosage unit formulations containing pharmaceutically acceptable carriers, adjuvants and vehicles. Parenteral administration can involve subcutaneous injections, intravenous or intramuscular injections or infusion techniques. Injectable liquids can include aqueous and/or organic components. Treatment duration can be as long as deemed necessary by a treating physician. The compositions can be administered as often as needed, e.g., one to four (or more) or more times per day. Administration can take place twice daily, thrice daily, daily, weekly, biweekly, twice weekly, every other week, monthly, and the like. A treatment period can terminate when a desired result, for example, a particular therapeutic effect, is achieved. However, in some instances, a treatment period can be continued indefinitely.

In some embodiments, pharmaceutical compositions can be prepared as solid dosage forms for oral administration (e.g., capsules, tablets, pills, dragees, powders, granules and the like). Tablets can be prepared by compression and/or molding. Compressed tablets can include pharmaceutically acceptable excipients, such as, but not limited to, binders, lubricants, glidants, inert diluents, preservatives, disintegrants, and dispersing agents. Tablets and other solid dosage forms, such as, but not limited to, capsules, pills, powders, and granules, can include coatings, such as enteric coatings.

Liquid dosage forms for oral administration can include, for example, vehicles such as, but not limited to, pharmaceutically acceptable emulsions, microemulsions, solutions, suspensions, syrups and elixirs. The liquid vehicles can have aqueous and/or organic components. Suspensions can include one or more suspending agents. Examples of ingredients useful in liquid dosage forms include, but are not limited to, chelants, sequestering agents, viscosifiers, thickeners, penetration enhancers, solvents, emulsifiers, and emollients.

Pharmaceutical compositions suitable for parenteral administration can include the spirocyclic compound together with one or more pharmaceutically acceptable sterile isotonic aqueous or non-aqueous solutions, dispersions, suspensions or emulsions.

Alternatively, the composition can be in the form of a sterile powder that can be reconstituted into a sterile injectable solutions or dispersion just prior to use.

Solid and liquid dosage forms can be formulated such that they conform to a desired release profile, e.g., immediate release, delayed release, and extended or sustained release.

The amount of spirocyclic compound to be administered will vary depending on factors such as the following: the spirocyclic compound selected, method of administration, release profile, and composition formulation. Typically, for the two spirocyclic compounds, in an oral dosage form to treat or prevent PAH/APAH, a typical dosage will be about 1 mg/kg/day to about 50 mg/kg/day and more typically from about 5 mg/kg/day to about 30 mg/kg/day, based on the weight of the patient. A most preferred spirocyclic compound is RVT-1201 in crystalline Form 3. Individual oral dosage forms typically have from about 50 mg to about 3000 mg of a spirocyclic compound and additional amounts of one or more pharmaceutically acceptable excipients. Other useful individual oral dosage forms can, by way of example, have spirocyclic compound in amounts of 100 mg, 150 mg, 200 mg, 250 mg, 300 mg, 350 mg, or 400 mg, 450 mg, 500 mg, 550 mg, 575 mg, 600 mg, 625 mg, 650 mg, 675 mg, 700 mg, 725 mg, 750 mg, 775 mg, 800 mg, 900 mg, 950 mg, 1000 mg, 1050 mg, 1100 mg, 1150 mg, and about 1200 mg, particularly 1200 mg. A preferred dosage is 1200 mg. Other amounts between 50 mg to 3000 mg are possible, for example, from about 325 mg to about 475 mg, from about 350 mg to about 500 mg, from about 375 to about 525 mg, from about 400 mg to about 550 mg, from about 425 mg to about 575 mg, from about 450 mg to about 600 mg, from about 475 mg to about 625 mg, from about 500 mg to about 650 mg, from about 525 mg to about 675 mg, from about 550 mg to about 700 mg, from about 575 mg to about 725 mg, from about 600 mg to about 750 mg, from about 625 mg to about 775 mg, from about 650 mg to about 800 mg, from about 675 mg to about 825 mg, from about 700 mg to about 850 mg, from about 725 mg to about 875 mg, from about 750 mg to about 900 mg, from about 775 mg to about 925 mg, from about 800 mg to about 950 mg, from about 825 to about 975, from about 850 mg to about 1000 mg, from about 900 mg to about 1150 mg, from about 1000 mg to about 1150 mg, from about 1100 mg to about 1250 mg, and from about 1200 mg to about 1350 mg.

"wt %" means weight percent based on the total weight of the composition or formulation.

According to the present disclosure, there is also provided a method of treating or preventing PAH/APAH in a patient by administering to the patient a therapeutically effective amount of a THP1 inhibitor in the methods of administration and dosing levels described above. Further according to the present disclosure, there are also provided compositions, e.g., pharmaceutical compositions, useful for the treatment of PAH and/or APAH, and methods to treat PAH and/or APAH with such compositions. The composition comprises one or more TPH1 inhibitors disclosed herein, and one or more pharmaceutically acceptable excipients.

The compositions of the present invention may comprise 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, 450 mg, 460 mg, 470 mg, 480 mg, 490 mg, 500 mg, 510 mg, 520 mg, 530 mg, 540 mg, 550 mg, 560 mg, 570 mg, 580 mg, 590 mg, 600 mg, 610 mg, 620 mg, 630 mg, 640 mg, 650 mg, 660 mg, 670 mg, 680 mg, 670 mg, 680 mg, 690 mg, 700 mg, 710 mg, 720 mg, 730 mg, 740 mg, 750 mg, 760 mg, 770 mg, 780 mg, 790 mg, 800 mg, 810 mg, 820 mg, 830 mg, 840 mg, 850 mg, 860 mg, 870 mg, 880 mg, 890 mg, 900 mg, 910 mg, 920 mg, 930 mg, 940 mg, 950 mg, 960 mg, 970 mg, 980 mg, 990 mg, 1000 mg, 1050 mg, 1100 mg, 1150 mg, 1200 mg, 1250 mg, 1300 mg, 1350 mg, or 1400 mg of one or more TPH1 inhibitors disclosed herein, and, additionally, one or more pharmaceutically acceptable excipients.

The compositions of the present invention may comprise from about 10 mg to about 3000 mg and especially about 10 mg to about 1200 mg of one or more TPH1 indicators disclosed herein, and one or more pharmaceutically acceptable excipients.

The spirocyclic compounds described above and pharmaceutically acceptable salts thereof are useful THP1 inhibitors. Other useful THP1 inhibitors include phenylalanine-derived TPH1 inhibitors, such as p-chlorophenylalanine and p-Ethynyl phenylalanine, See "p-Ethynylphenylalanine: A Potent inhibitor Of Tryptophan Hydroxylase", *Journal of Neurochemistry* 74, 2067-73 (2000). Other useful THP1 inhibitors include substituted 3-(4-(1,3,5-triazin-2-yl)-phenyl)-2-aminopropanoic acids. See "A Tryptophan 5-hydroxylase Inhibitor, And its Potential In Chronic Diarrhea Associated With Increased Serotonin", *Neurogastroenterology and Motility: The Official Journal of The European Gastrointestinal Motility Society* 23, 193-200 (2011); "Substituted 3-(4-(1,3,5-triazin-2-yl)-phenyl)-2-aminopropanoic Acids As Novel Tryptophan Hydroxylase Inhibitors" *Bioorganic & Medicinal Chemistry Letters* 19, 5229-32. (2009); "Modulation Of Peripheral Serotonin Levels By Novel Tryptophan Hydroxylase inhibitors For The Potential Treatment Of Functional Gastrointestinal Disorders" *Journal of Medicinal Chemistry* 51, 3684-7 (2008); and "Discovery And Characterization of Novel Tryptophan Hydroxylase Inhibitors that Selectively inhibit Serotonin Synthesis in the Gastrointestinal Tract", *The Journal of Pharmacology and Experimental Therapeutics*, 325, 47-55 (2008)).

EXAMPLES

The following are examples of the disclosure and are not to be construed as limiting.

Example 1

In rat, orally administered RVT-1201 at a dose of 100 mg/kg/day (KAR5417 $AUC_{0-24}$ 15,300 ng·h/mL) may block or ameliorate PAH in both a monocrotaline prevention model and a SUGEN-hypoxia treatment model for established PAH. RVT-1201 (30 to 300 mg/kg/day) may yield a dose-dependent reduction in rat serum serotonin (-27% to -96%) and 24 h urinary output of 5-HIAA (-45% to -56%). HIAA is a metabolite that reflects total serotonin biosynthesis.

Divided dose studies in rats given 75 mg/kg/day (~65% serotonin reduction) may demonstrate KAR5417 $AUC_{0-24}$, rather than $C_{max}$ or $C_{trough}$, correlated with lowered serotonin biomarkers. Once daily administration to rats may show it is comparable to BID or TID regimens.

Example 2

Healthy human subjects (n=~120) may receive RVT-1201. Of treatment emergent adverse events received, none will be serious, nor considered a dose limiting toxicity. With standard meals, AUC following single doses will appear proportional to dose of 200 to ~1200 mg).

At 400 mg BID (twice daily), changes in 5-HIAA will be comparable across studies. Mean change in plasma 5-HIAA may be about -53% from Day 1 to Day 14, whereas placebo may be about +26%. Interpolation of KAR5417 AUC between 400 mg and 800 mg BID regimens may show 500-600 mg BID in humans will achieve the target exposure associated with efficacy in rat models. In summary, RVT-1201 may be well tolerated in healthy subjects at doses required to achieve clinically-relevant AUC, and lowering of serotonin biomarkers for treatment of PAH.

It should be understood that the foregoing description is only illustrative of the present disclosure. Various alternatives and modifications can be devised by those skilled in the art without departing from the present disclosure. Accordingly, the present disclosure is intended to embrace all such alternatives, modifications and variances which fall within the scope of the appended claims.

What is claimed is:

1. A method of inhibiting the formation of 5-HT in a human patient comprising:
   administering to the patient a therapeutically effective amount of a compound of (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate or a pharmaceutically acceptable salt thereof, wherein the compound is in substantially crystalline form, and
   wherein the therapeutically effective amount is about 1 mg/kg/day to about 50 mg/kg/day.

2. The method of claim 1, wherein the compound or pharmaceutically acceptable salt thereof is administered orally.

3. The method of claim 2, wherein the compound or pharmaceutically acceptable salt thereof is administered orally by a dosage form selected from the group consisting of capsules, tablets, powders, and granules.

4. The method of claim 1, wherein the compound or pharmaceutically acceptable salt thereof is administered one to four times per day.

Figure 2:
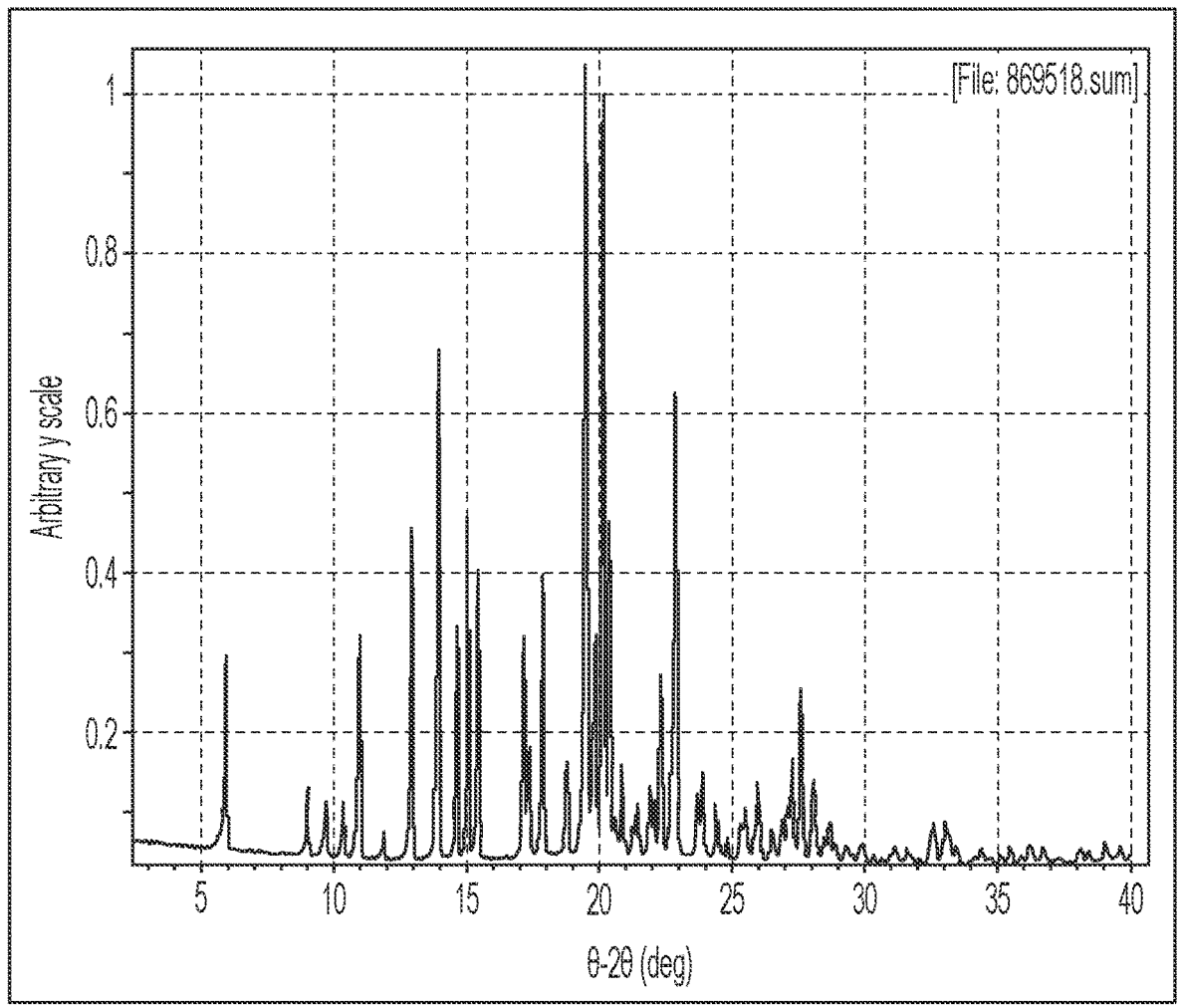
FIG. 2 is a plot of an XRPD of a crystalline compound of (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate of a different polymorphic form than that of FIG. 1 (crystalline Form 1).

5. The method of claim 1, wherein the compound is a crystalline polymorph characterized by an XRPD plot substantially as depicted in FIG. 1.

6. The method of claim 1, wherein the compound is a crystalline polymorph having a XRPD plot corresponding to Table 1 or Table 2.

7. The method of claim 1, wherein the compound is a crystalline polymorph exhibiting a characteristic XRPD peak at 19.05±0.20 (° 2°).

8. The method of claim 1, wherein the therapeutically effective amount is about 5 mg/kg/day to about 30 mg/kg/day.

* * * * *